(12) United States Patent
Koski et al.

(10) Patent No.: US 11,023,813 B2
(45) Date of Patent: Jun. 1, 2021

(54) GENETIC ALGORITHM WITH DETERMINISTIC LOGIC

(71) Applicant: nMetric, LLC, Dallas, TX (US)

(72) Inventors: Christine Koski, Dallas, TX (US); Stephen Cook, Albuquerque, NM (US); Ryan Heaton, Castle Rock, CO (US); Jonathan Watts, Denver, CO (US)

(73) Assignee: nMetric, LLC, Dallas, TX (US)

( * ) Notice: Subject to any disclaimer, the term of this patent is extended or adjusted under 35 U.S.C. 154(b) by 0 days.

(21) Appl. No.: 16/597,155

(22) Filed: Oct. 9, 2019

(65) Prior Publication Data

US 2021/0110281 A1 Apr. 15, 2021

(51) Int. Cl.
*G06N 5/04* (2006.01)
*G06Q 10/06* (2012.01)
*G06N 3/12* (2006.01)

(52) U.S. Cl.
CPC .............. *G06N 5/04* (2013.01); *G06N 3/126* (2013.01); *G06Q 10/06316* (2013.01)

(58) Field of Classification Search
CPC .................. G06N 3/126; G06Q 10/06; G06Q 10/063112; G06Q 10/06313; G06Q 10/06316; G06Q 10/0639; G06Q 10/1097; Y04S 10/54
See application file for complete search history.

(56) References Cited

U.S. PATENT DOCUMENTS

| 5,319,781 A | 6/1994 | Syswerda |
| 5,848,403 A | 12/1998 | Gabriner et al. |
| 2008/0244584 A1 | 10/2008 | Smith et al. |
| 2019/0220792 A1 | 7/2019 | Koski et al. |

FOREIGN PATENT DOCUMENTS

| KR | 10-2018-0065840 A | 6/2018 |
| NO | 2014-079678 A1 | 5/2014 |

OTHER PUBLICATIONS

Jain et al. "Production scheduling/rescheduling min flexible manufacturing", IJPR, 1997, pp. 281-309.*

(Continued)

*Primary Examiner* — Li Wu Chang
(74) *Attorney, Agent, or Firm* — Fish IP Law, LLP

(57) ABSTRACT

In a method for applying deterministic logic to select resources for resource genomes in a genetic algorithm, a logic engine identifies resources associated with an objective and an overall task population to be completed by one or more of the identified resources. The logic engine then selects a deterministic logical framework from one or more deterministic logical frameworks based on the objective. Following the selection of a deterministic logical framework, the logic engine selects one or more resources from the one or more identified resources based on the selected deterministic logical framework. The logic engine compiles the one or more selected resources into a resource genome, assigns one or more tasks from the task population to the one or more selected resources, and sends instructions to the one or more selected resources to execute the one or more tasks. The logic engine determines a value score for the resource genome.

7 Claims, 2 Drawing Sheets

(56) References Cited

OTHER PUBLICATIONS

Ying et al. "Job-Shop Scheduling Using Genetic Algorithm", ICSMM, 1996, pp. 1994-1999.*
Aydemir et al. "A New Production Scheduling Module Using Priority-Rule Based Genetic Algorithm", IJSM, 2015, pp. 450-462.*
Feng et al. "A Framework of Joint Energy Provisioning and Manufacturing Scheduling in Smart Industrial Wireless Rechargeable Sensor Networks", Sensors, 2018, p. 18.*
Van Peteghem et al. "A genetic algorithm for the preemptive and non-preemptive multi-mode resource-constrained project scheduling problem", EJOR, 2010, pp. 409-418.*
International Search Report and Written Opinion dated Jan. 29, 2021 for International Application No. PCT/US2020/055092; 9 pages.

* cited by examiner

GENETIC ALGORITHM WITH DETERMINISTIC LOGIC

FIELD OF THE INVENTION

The field of the invention is scheduling systems.

BACKGROUND

When a company has a series of resources available to carry out tasks, a manager typically determines which resource (e.g., employees, manufacturing equipment, etc.) is used to execute one or more tasks. Computer scheduling systems, for example Microsoft Outlook®, can be helpful to visualize such resource availability. For example, a scheduler could use a computer scheduling system to block off specific resources to perform certain tasks, and assign specific resources to specific tasks. Each resource would then have a calendar of tasks to do throughout each day, week, and month, which could be easily visualized and organized. In order for a scheduler to assign specific employees to each task, however, the manager needs to manually track each resource and allocate each resource to the appropriate task.

A scheduler not only needs to determine how to schedule and allocate resources, but also needs to determine characteristics of each resource in order to maximize the efficiency of resource allocation. For example, a scheduler can schedule the use of a particular resource to particular tasks in between prescheduled jobs by determining which resources have the largest gap between the previous task and the subsequent task, which allows additional tasks to be woven into a resource schedule. Each task would then be allocated to resources based on one or more characteristics of the resource in order to increase the overall efficiency of the system. However, the number of combinations of particular resource allocation and resource priorities is often far too numerous for a human to test all the combinations in order to maximize efficiency. Additionally, a large number of combinations can produce multiple possible combinations of task allocations and task priorities sufficient to complete the task. Lastly, the step of allocating resources to tasks based on resource characteristics adds an undesirable variable because it introduces human judgment/human error into the system.

Genetic algorithms can explore a larger search space that a human, or indeed than other routines, to find a maximally efficient resource allocation schedule. However, since purely genetic algorithms create, recombine, and mutate genomes (e.g., resource allocation schedules) randomly to attempt to find increasingly efficient genomes for recombination and/or mutation, genetic algorithms can take significant amounts of time to find an optimal resource allocation schedule. Additionally, conventional genetic algorithms can produce genomes that, when recombined, prematurely converge to a local minima over time that is tightly related with a loss of genetic diversity within a population of genomes. Thus, conventional genetic algorithms take significant resources to come to an optimal solution and can be further hindered from finding an optimal solution because of premature convergence to a local minima.

The prior art recognizes the problem of convergence to a local minima in conventional genetic algorithms, and attempts to correct the problem after it has occurred. There seems to be no teaching, suggestion or motivation in the prior art to apply deterministic logic to genetic algorithms to prevent the problem of premature convergence to a local minima from occurring in the first place.

U.S. Pat. No. 5,319,781 to Syswerda teaches a computer implemented method for managing task allocation in one or more genetic algorithms based on hard and soft task constraints. Syswerda, however, discloses a method that uses hard and soft constraints associated with the task, instead of the resource. As such, Syswerda requires significant resources to converge to an optimal solution because variables associated with each task must be considered in arriving at an optimal solution, which, in genetic algorithm-based systems and conventional systems, far exceeds the number of resources. However, Syswerda does not fully address the inefficiencies of genetic algorithms because the guided evolution of a task-based genome is associated with a very large search space compared to a search space limited to resources.

U.S. Pat. No. 5,848,403 to Gabriner teaches a computer system for managing a scheduling system, wherein the system matches a task constraint to a resource capability to determine whether or not a task can be completed. The system then matches available resources with the task in order to accomplish the task. Gabriner's computer system, however, fails to focus on resource constraints in determining a schedule using a genetic algorithm. Gabriner describes a conventional genetic algorithm that does not use deterministic logic.

Syswerda, Gabriner, and all other extrinsic materials discussed herein are incorporated by reference to the same extent as if each individual extrinsic material was specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for genetic algorithms enhanced with a deterministic logical framework to prevent a genetic algorithm from prematurely converging to a local minima.

SUMMARY OF THE INVENTION

A resource-orientated computer system allows a schedule to calendar tasks based on resource-constraints (e.g., people, equipment, tools, rooms, virtual rooms, computers, etc) by using deterministic logical framework to focus on the attributes of the resources to converge towards an optimized solution without having the genome prematurely converge to a local minima. Another aspect of the inventive subject matter is appreciation (either self-generated or by receiving information from another) that it is even possible to prevent a genetic algorithm from prematurely converging to a local minima.

By focusing on systems and methods that prevent a genetic algorithm from prematurely converging to a local minima, it is thought that the currently claimed subject matter is nonconventional and not routine.

As used herein, premature convergence means that the parental population of genes for an optimization problem falls below a threshold genetic diversity, resulting in offspring genes that are unable to outperform the parent genes.

Among other things, the inventive subject matter provides apparatus, systems, and methods in which a genetic algorithm recombines and mutates task schedules with resource attributes and applies deterministic logical framework in order to increase the overall efficiency of the system in arriving at the optimal solution rather than converging prematurely to a less efficient schedule. As used herein, a "resource" is any resource, whether physical or virtual, living or nonliving. Examples include a room, a building, a consumable item, a portable tool, a piece of equipment that is fixed to a location, a person, or an animal. Each resource typically has a series of unique and non-unique attributes that are associated with the resource. As the terms imply, unique attributes are attributes that are unique to that particular resource, and non-unique attributes are attributes that can be common by more than one resource. For example, if the resource is a only available at particular times of the week (e.g. an individual or a machine that has limited availability), then the weekly availability of the resource is an attribute of the resource. As used herein "jobs" refers to subsets of one or more tasks that are required to achieve an overall objective.

Various resources, features, aspects and advantages of the inventive subject matter will become more apparent from the following detailed description of preferred embodiments, along with the accompanying drawing figures in which like numerals represent like components.

The present invention advantageously prevents genetic algorithms from prematurely converging to a local minima by applying deterministic logic.

DETAILED DESCRIPTION

It should be noted that while the following description is drawn to a computer-based scheduling system, various alternative configurations are also deemed suitable and may employ various computing devices including servers, interfaces, systems, databases, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclose apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including facilitating the scheduling of events, facilitating the efficient manufacture of one or more goods, and any other application of genetic algorithms known in the art.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figure 1:
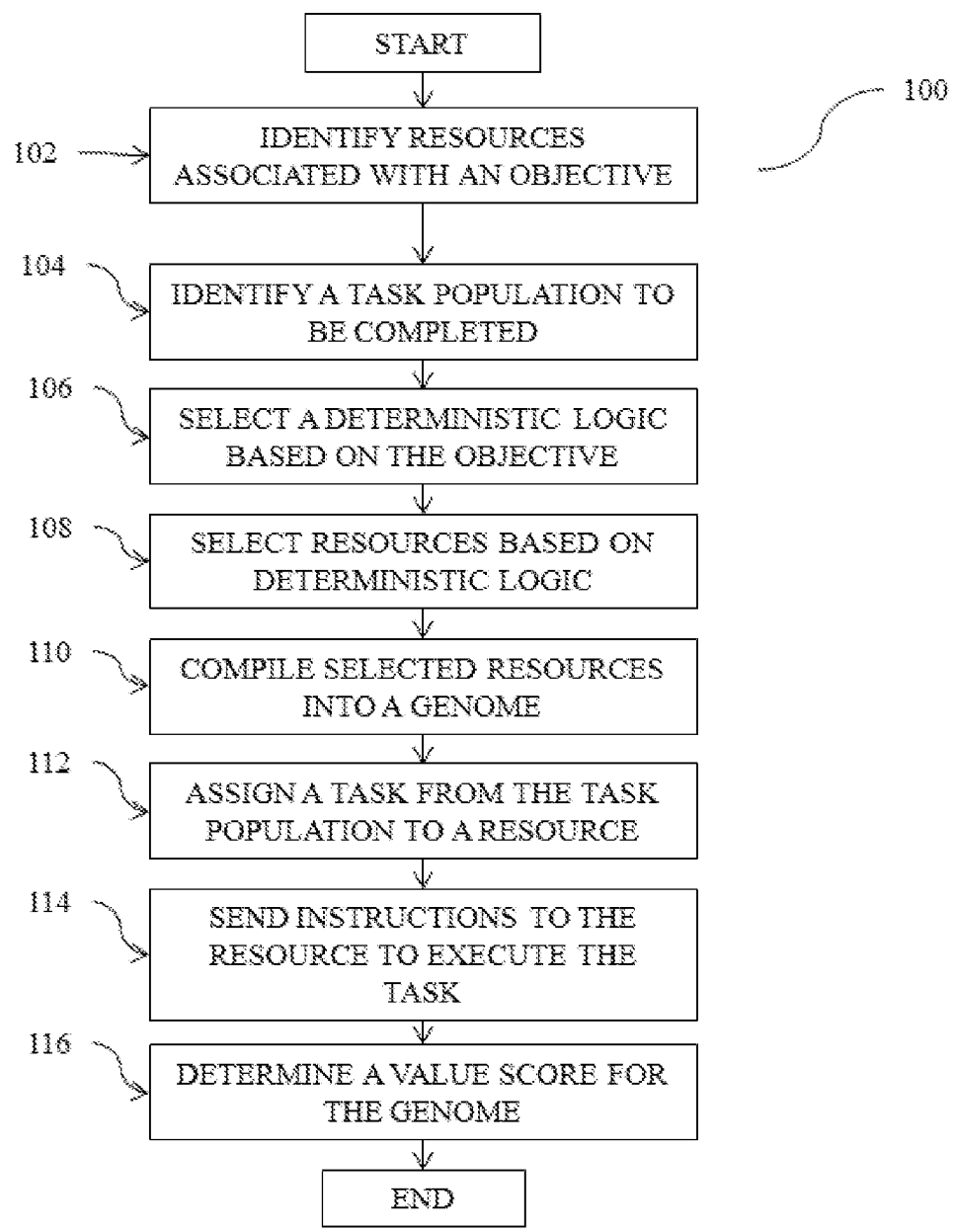
FIG. 1 is a schematic of a method of selecting and applying a deterministic logical framework to resource selection in creating a resource genome.

FIG. 1 is a schematic of a method of selecting and applying a deterministic logical framework to resource selection in creating a resource genome.

Logic engine 100 identifies one or more resources associated with an objective (step 102).

As defined herein, an objective refers to any end goal achievable through the execution of one or more tasks using one or more resources. Tasks are any actions required to achieve an objective, such as a job or the manufacture of a good. An objective can comprise multiple tasks. For example, in scheduling the production of a widget, each objective is associated with the fabrication of a sub-component of the widget, and the fabrication of the subcomponents of the widget each comprises multiple tasks.

Logic engine 100 uses one or more precompiled lists of resources associated with the objective. In another embodiment, logic engine 100 determines one or more resources from the available resources based on at least one variable associated with the resources and the overall objective. For example, logic engine 100 can determine which resources will be necessary to achieve the overall objective based on the constituent parts in a widget and the manufacturing resources necessary to fabricate each component of the widget.

Alternatively, logic engine 100 uses machine learning techniques to analyze historical trends to predict which available resources are required to achieve an overall objective. For example, logic engine 100 can use a supervised learning classifier to infer a function from labeled training data (e.g., set of training examples). In another example, logic engine 100 uses time-series forecasting to determine maximize the concurrent execution of tasks by one or more resources to minimize the amount of time to achieve the overall objective. It is contemplated that logic engine 100 can use any technique known in the art to identify one or more jobs associated with the overall objective.

Logic engine 100 identifies a population of tasks to be completed (step 104).

Tasks comprise any action required to complete a job. For example, logic engine 100 can identify that a quality control step is required to complete the construction of an automobile motor and generate a population of tasks that are associated with the quality control step, such as checking raw power output, confirming proper power bands using a dynamometer, and verifying correct compressions levels in the cylinders.

Logic engine 100 selects a deterministic logical framework based on the objective to apply to a resource genome (step 106).

Deterministic logical frameworks can comprise any logic that guides the execution of a task, such as one or more overall priorities associated with the objective.

For example, deterministic logical frameworks can comprise one or more of: (1) most resource utilization in a time frame, (2) least resource utilization in a time frame, (3) shortest time gap from completing a previous task to starting a subsequent task for a resource, (4) longest time gap from completing a previous task to starting a subsequent task for a resource, (5) re-use of a resource on a job, (6) exclusion of resources on a job, (7) resource costs to execute a task, (8) resource efficiency in executing a task, and (9) the proximity of a first resource to a second resource in a task progression to achieve an objective.

However, the contemplated subject matter is not limited to the aforementioned deterministic logical frameworks and can include any deterministic logical framework known in the art, either individually or in combination. Resources can comprise anything that is used to complete a task to achieve an objective. For example, resources can include, but are not limited to, people, machines, tools, supplies, software, and consumable resources.

In one embodiment, logic engine 100 selects a deterministic logical framework based on user-selected objectives. For example, a user can prioritize speed over accuracy in a manufacturing task requiring less precision, such as, for example, the manufacture of foam fillers for shipping. In this example, logic engine 100 can select and use the deterministic logical framework of the smallest time gap between completing a previous task and starting a subsequent task to guide the selection of resources that are capable of quickly executing manufacturing tasks.

In an alternative embodiment, logic engine 100 automatically decides which deterministic logical framework to apply based on one or more parameters associated with the overall objective. For example, logic engine 100 can apply the deterministic logical framework of selecting resources based on the least utilization in a manufacturing time frame based on a manufacturing objective that requires high levels of precision and minimization of manufacturing failure rates, such as, for example, the manufacture of specialized medical devices.

By applying deterministic logic to resource genomes, the resource scheduling search space can advantageously be more fully explored than by pure genetic algorithms, which can prematurely converge to a local minima. Additionally, applying deterministic logic advantageously save significant amounts of time in finding increasingly better resource schedules by allowing logic engine 100 to focus on relevant priorities. For example, logic engine 100 can target resources that maximize production speed without having to explore resource genomes that prioritize low manufacturing failure rates in simple manufacturing applications that do not require high precision.

Logic engine 100 selects one or more resources using the deterministic logic (step 108). In one embodiment, where the deterministic logic prioritizes minimizing the amount of time between completion of a previous task to starting a subsequent task, logic engine 100 selects a group of resources that are in closest proximity to each other based on a manufacturing order. Logic engine 100 can thereby compile resources that increase efficiency by reducing movement time of manufacturing intermediates from a first resource completing a first manufacturing process to a second resource starting a subsequent manufacturing process.

In yet another embodiment, where the deterministic logic prioritizes maximizing the amount of time between completion of a previous task to starting a subsequent task, logic engine 100 selects a group of resources with greater distances than necessary between each other to increase the movement time of manufacturing intermediates between resources. For example, in manufacturing applications, logic engine 100 can select resources that are far away enough from each other to allow resource intermediates requiring a minimum amount of time to cure (e.g., concrete, glues, etc.) to fully set before the next manufacturing step.

It is also contemplated that logic engine 100 can select resources based on deterministic logic applied to overall service objectives. For example, logic engine 100 can select medical professionals, which are considered the resources, for a high-risk surgery with the highest success rates by applying deterministic logic that selects resources based on lowest available failure rates. In this example, the inventive subject matter can be adjusted to adapt to strategies that may be counter-intuitive in one field but valuable in others.

Logic engine 100 compiles the selected one or more resources into a resource genome (step 110).

The resource genome defines a resource schedule based on the deterministic logical framework applied by logic engine 100. Logic engine 100 can designate particular resources as being unaffected by particular deterministic logical frameworks, thereby allowing them to be incorporated into any resource genome that limits the selected resources based on the particular deterministic logical frameworks. For example, logic engine 100 can designate a resource that completes an electroplating step (requiring the same amount of time to complete regardless of the dimensions of the item and being able to carry out multiple electroplating steps for multiple resource genomes simultaneously) as being unaffected by the time between completion of a previous task and a subsequent task.

In some embodiments, logic engine 100 applies multiple deterministic logical frameworks to a list of resources to select and compile resources into a resource genome. In preferred embodiments, logic engine 100 applies one deterministic logical framework to a list of resources to select and compile resources into a resource genome. In such embodiments, it is contemplated that different resource genomes selected based on different deterministic logical frameworks can be mutated, recombined, and/or manipulated in any way known in the art. It is also contemplated that resource genomes compiled based on multiple deterministic logical frameworks can be mutated, recombined, and/or manipulated in any way known in the art. In one example, logic engine 100 can choose to recombine a first resource genome for a manufacturing process prioritizing minimal manufacturing times with a second resource genome prioritizing lowest resource failure rate in order to attempt to produce a resource genome that balances high speed and high precision.

Logic engine 100 assigns a task from the task population to a selected resource (step 112).

It is contemplated that logic engine 100 assigns each task for execution directly in a fully automated system. For example, logic engine 100 can send program instructions to cause manufacturing resources (e.g., automated manufacturing robots) to execute each task. It is also contemplated that logic engine 100 instructs one or more individuals to carry out each task. For example, logic engine 100 can instruct multiple machinists to carry out each task associated with the manufacture of an automobile engine block in a manner designated by logic engine 100. However, logic engine 100 is not limited to purely automated or purely user-based systems and can cause execution each task by any means or combination of means available.

Logic engine 100 sends instructions to the selected resource to execute the task (step 114).

It is contemplated that logic engine 100 can send instructions directly to a selected resource. In some embodiments, instructions sent to a selected resource are automatically executed. For example, a manufacturing resource can automatically initiate a manufacturing process based on instructions received from logic engine 100. In other embodiments, logic engine 100 can send instructions to a selected resource which can independently initiate completion of the task within the parameters of the instructions. For example, a manufacturing resource can receive instructions from logic engine 100 to initiate a manufacturing process and complete the process within a designated time frame. The manufacturing resource can then initiate the manufacturing process at a later time within the parameters of the instructions (e.g., initiate manufacturing process after Step 5 or initiate and complete manufacturing process between 8:00 AM and 10:00 AM). In another example, a car mechanic can receive instructions from logic engine 100 to complete a tire rotation for a particular vehicle before 12:00 PM that day. The car mechanic can then choose to complete the service at any time before 12:00 PM that day.

Logic engine 100 determines a value score for the resource genome (step 116).

A value score indicates the overall success of a genome in achieving one or more metrics, such as completion time, accuracy of the process, and production costs. Logic engine 100 preferably determines the value score for the resource genome using a fitness function. A fitness function is a particular type of objective function that is used to summarize, as a single figure of merit, how close a given solution is achieving the set aims. Once logic engine 100 determines the value score of a resource genome, the resource genome can be discarded, mutated, or recombined with other resource genomes.

Figure 2:
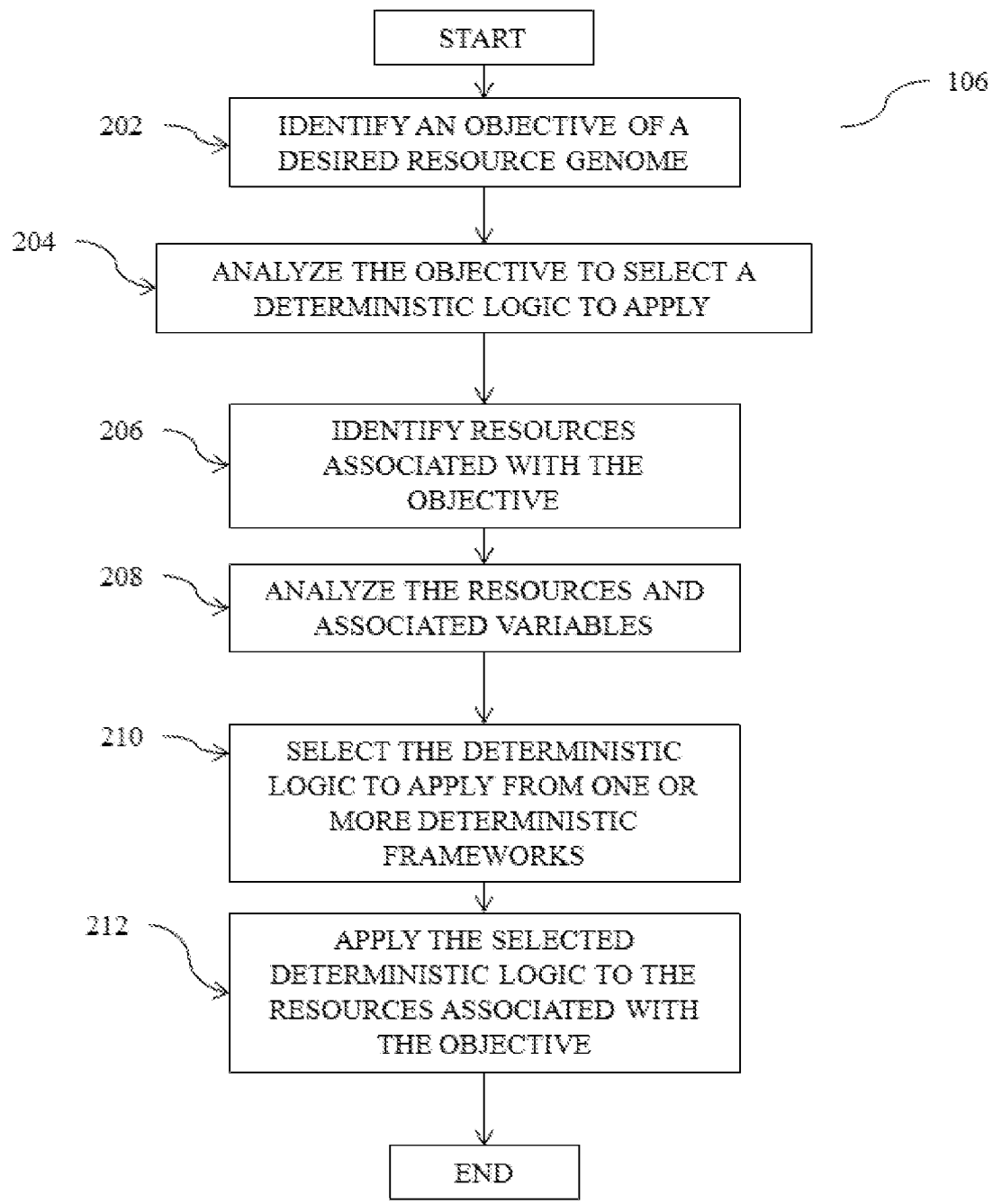
FIG. 2 is a schematic of a method of selecting resources based on a selected deterministic logical framework.

FIG. 2 is a schematic of a method of selecting resources based on a selected deterministic logical framework.

Logic engine 100 identifies an objective of a desired resource genome (step 202).

For example, in scheduling the production of a widget, the resource genome can comprise every available resource associated with the production of the widget. Resources can include any entity that is used to perform a task. For example, resources can include, but are not limited to, human services, manufacturing equipment, software, a consumable item, a consumable service, or any other resource. A resource genome comprises a compilation of resources that are used for the completion of one or more tasks associated with an overall objective.

Logic engine 100 uses one or more predetermined task lists associated with the overall objective to determine which resources are associated with the overall objective. Alternatively, logic engine 200 uses machine learning techniques to analyze historical trends to predict what jobs are necessary to achieve the overall objective. For example, logic engine 100 can use a supervised learning classifier to infer a function from labeled training data (e.g., set of training examples). In another example, logic engine 200 can use time-series forecasting to determine maximize the concurrent execution of jobs to minimize the amount of time to achieve the overall objective. It is contemplated that logic engine 100 can use any technique known in the art to identify one or more jobs associated with the overall objective.

Logic engine 100 analyzes the objective to select a deterministic logical framework to apply (step 204).

Tasks comprise any action required to complete a job. For example, logic engine 200 can identify that a quality control step is required to complete the construction of an automobile motor and generate a population of tasks that are associated with the quality control step, such as checking raw power output, confirming proper power bands using a dynamometer, and verifying correct compressions levels in the cylinders.

Logic engine 100 identifies one or more resources associated with the objective (step 206)

Logic engine 100 uses one or more precompiled lists of resources associated with the objective. In another embodiment, logic engine 100 determines one or more resources from the available resources based on at least one variable associated with the resources and the overall objective. For example, logic engine 100 can determine which resources will be necessary to achieve the overall objective based on the constituent parts in a widget and the manufacturing resources necessary to fabricate each component of the widget.

Alternatively, logic engine 100 uses machine learning techniques to analyze historical trends to predict which available resources are required to achieve an overall objective. For example, logic engine 100 can use a supervised learning classifier to infer a function from labeled training data (e.g., set of training examples). In another example, logic engine 100 uses time-series forecasting to determine which resources can be run concurrently to minimize the amount of time to achieve the overall objective. It is contemplated that logic engine 100 can use any technique known in the art to identify one or more resources associated with the overall objective.

Logic engine 100 analyzes the resources and variables associated with each of the resources (step 208).

It is contemplated that logic engine 100 analyzes the one or more variables associated with each resource to compile a resource genome that achieves a designated objective.

Variables can include any characteristic or collection of characteristics about a resource. In manufacturing processes, variables can include, but are not limited to, average completion time, success rates, failure rates, most utilization within a given time frame, least utilization within a given time frame, types of tasks that can be completed by the resource, and capacity to concurrently execute multiple tasks. In administering services, variables can include average completion time, success rates, failure rates, most utilization within a given time frame, least utilization within a given time frame, types of tasks that can be completed by the resource, capacity to concurrently execute multiple tasks, professional credentials, amount of relevant experience, and time frames when service providers are available.

Logic engine 100 selects a deterministic logical framework to apply from one or more deterministic logical frameworks (step 210).

For example, logic engine 100 can analyze the overall objective and apply the deterministic logical framework of selecting resources with the most completed tasks in a given time frame in order to prioritize speed over accuracy in a manufacturing task requiring less precision. For example, logic engine 100 can apply the aforementioned deterministic logical framework to manufacturing processes that produce cruder products, such as, for example, the manufacture of foam fillers for shipping. In an alternative example, logic engine 100 can select and use the deterministic logical framework of the smallest time gap between completing a previous task and starting a subsequent task to guide the selection of resources that are capable of quickly executing manufacturing tasks.

In an alternative embodiment, logic engine 100 automatically decides which deterministic logical framework to apply based on one or more parameters associated with the overall objective. For example, logic engine 100 can select resources based on the least utilization in a manufacturing time frame where the manufacturing objective necessitates high levels of precision and at low volumes, such as, for example, the manufacture of specialized medical devices.

Logic engine 100 applies the selected deterministic logical framework to the one or more resources associated with the objective (step 212).

Logic engine 100 advantageously selects each resource of a collection of resources that are required to complete all tasks associated with the overall objective. However, logic engine 100 can also receive specific instructions from an external entity, such as a user of logic engine 100, to guide the selection of resources. For example, a user can instruct logic engine 100 to ignore particular resources without significant limitations, such as resources capable of refining raw materials into large amounts of usable material, when compiling resource genomes.

Logic engine 100 then instructs one or more resource to carry out the tasks. Logic engine 100 can instruct a resource to carry out a task in a particular manner, such as, for example, at a particular time, at a particular speed, and in a particular order. For example, logic engine 100 can instruct multiple machinists to carry out each task associated with the manufacture of an automobile engine block in a particular order and within designated time frames. However, logic engine 100 is not limited to purely automated or purely user-based systems, and can cause execution of any task by any means or combination of means available.

Logic engine 100 determines a value score of the genome (step 214).

A value score indicates the overall success of a resource genome in achieving one or more metrics, such as completion time, accuracy of the process, and production costs. Logic engine 100 preferably determines the value score for the resource genome using a fitness function. A fitness function is a particular type of objective function that is used to summarize, as a single figure of merit, how close a given solution is achieving the set aims. Once logic engine 100 determines the value score of a resource genome, the resource genome can be discarded, mutated, or recombined with other resource genomes.

Task Scheduling Example

An administrator at a large hospital needs to schedule an open heart surgery, more specifically, an aortic valve replacement (i.e., the "task") for a patient that recently suffered a heart attack. The surgery requires one heart surgeon, one anesthesiologist, and at least three medical support staff, which include a surgical assistant, an equipment monitoring assistant, and a junior surgeon. The surgery also requires an operating room that can accommodate the size of the medical team during the four hour surgery, and that has the necessary equipment, tools, and consumables (e.g., human valve donor or a mechanical valve, blood transfusion machine, sufficient volume of blood for the transfusion, heart rate monitor, defibrillator, endoscopic video camera, surgical knives and other surgical tools, disinfectants, gauze, etc).

The administrator can use the genetic algorithm-based methods and systems disclosed herein in order to find the most efficient allocation of hospital staff based on their characteristics. The administrator enters the overall objective which is associated with multiple jobs into logic engine 100. The administrator designates a deterministic logical framework based on the overall objective and the particular details regarding the overall objective. The deterministic logical framework selected by the administrator allows logic engine 100 to select resources that best achieve parameters defined by the selected deterministic logical framework. For example, where a deterministic logical framework prioritizes overall success rate, logic engine 100 can select resources with the highest success rates for the cardiothoracic surgeon and the vascular surgeon while selecting the janitor, the surgical assistant, and the junior surgeon based on a minimum amount of time that the support staff has worked with the selected surgeons, respectively. Additionally, logic engine 100 can instruct each resource to carry out specific tasks in specific ways. For example, logic engine 100 can instruct the surgical assistant to compile specific amounts/numbers of consumables (e.g., syringes, saline, gauze, blood, etc.) in the surgery room. Once the objective is completed, logic engine 100 determines a value score for the resource genome, which, in preferred embodiments, how successful the resource genome was in achieving the objective.

In this example, the use of the genetic algorithm-based methods and systems disclosed herein avoids premature convergence by directing the genetic evolution away from suboptimal genes (e.g., genes representing resources that produce inefficient or unacceptable results). As such, each generation of offspring is guaranteed to contain genes representing resources that at least meet a threshold viability in achieving one or more desired outcomes.

Where the medical procedure is a simple injection of a vaccine, and the selected deterministic logical framework prioritizes shortest completion time from start to finish, logic engine 100 could select medical staff with the highest completed medical appointments within a given time frame.

Unlike the presently described scheduling system, conventional scheduling systems using genetic algorithms would search a significantly larger search space with randomized priorities to attempt to arrive at a logical conclusion. As such, conventional scheduling systems using genetic algorithms without deterministic logic can waste large amounts of computing resources and create inferior schedules by converging to a local minima. A local minima represents the evolution of a gene pool being limited to a smaller subset of inferior genes without the ability to be evolve out of an inferior state because superior genes have been filtered out of the gene pool.

By guiding a genetic algorithm in a relevant direction to the objective at hand, irrelevant resource genomes are filtered out much more quickly. In the example above, logic engine 100 would not have to explore a search space for resources that have quick completion rates for a heart surgery requiring precision and long operating hours, which drastically reduces the amount of processing power and time required for logic engine 100 to arrive at an optimized resource schedule.

Recombination Example

Once the task scheduling example has been completed multiple times, and created various genomes each associated with value scores, logic engine 100 can select two resource genomes with similar value scores. Preferably, logic engine 100 can select the two highest scoring resource genomes to recombine. Alternatively, recombination engine 300 can select the highest scoring resource genome guided by a first deterministic logical framework and recombine it with a highest scoring resource genome for a guided by a second deterministic logical framework, where the second deterministic logical framework is different from the first. For example, recombination engine 300 can select a first resource genome compiled to achieve the quickest manufacturing time for a widget and recombine it with a second resource genome compiled to achieve the highest success rate per resource.

Over many cycles of recombination and subjecting resource genomes to fitness evaluations, the method achieving an overall objective is continuously refined to eventually yield the most effective solution based on one or more deterministic logical frameworks. This recombination example illustrates how the inventive methods and systems described herein go significantly beyond coordinating the availability of specific people or resources. Rather, logic engine 100 automates the resource compilation process to discover the most effective way of achieving an overall objective by using the principles of genetic recombination and evolution and related fitness functions.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for applying deterministic logic to select resources for resource genomes in a genetic algorithm to prevent premature convergence to a local minima, comprising:
   identifying resources associated with an objective;
   identifying overall task population to be completed by one or more of the identified resources;
   executing, by a logic engine, a time-series forecasting analysis, wherein the logic engine is further configured to:
   analyze historical resource timing data associated with the resources and associated tasks;
   determine timing characteristics for each of the resources, wherein the timing characteristics include predicting an expected time gap from the completion of a previous task to starting a subsequent task;
   analyzing, based at least in part on the time-series forecasting analysis, one or more deterministic logical frameworks associated with the identified resources, the objective, and the overall task population;
   selecting a deterministic logical framework from the one or more deterministic logical frameworks based on the time-series forecasting;
   selecting one or more resources from the one or more identified resources based on the selected deterministic logical framework;
   compiling the one or more selected resources into a resource genome;
   assigning one or more tasks from the task population to the one or more selected resources, wherein the assignment of tasks to the one or more selected resources is configured to minimize an amount of time required to achieve the objective;
   sending instructions to the one or more selected resources to execute the one or more tasks; and
   determining a value score for the resource genome, wherein the value score represents a measure of success in minimizing time to reach the objective.

2. The method of claim 1, wherein the deterministic logical framework defines a selection criterion that is applied to the identified resources associated with the objective.

3. The method of claim 2, wherein the deterministic logical framework is selected from the group consisting of: a most utilized resource within a time frame, a least utilized resource within the time frame, a shortest time gap from completing a previous task to starting a subsequent task, a longest time gap from completing the previous task to starting the subsequent task, a reused resource in multiple tasks, an excluded resource for the multiple tasks, a resource operating cost, a resource efficiency measurement, and a resource proximity within a task progression.

4. The method of claim 1, further comprising analyzing one or more variables associated with the identified resources, wherein the one or more variables are associated with at least one resource capability.

5. The method of claim 1, further comprising:
   recombining the resource genome with a second resource genome, wherein the second resource genome is associated with a second value score; and
   determining a third value score for the recombined resource genome.

6. The method of claim 1, wherein the value score is determined using a fitness function, and wherein the fitness function summarizes how close the resource genome is to achieving the objective as a single figure of merit.

7. The method of claim 1, wherein the resource is selected from the group consisting of: a human, a machine, and a consumable resource.

* * * * *